(12) United States Patent
Rosenbluh et al.

(10) Patent No.: US 12,059,445 B2
(45) Date of Patent: Aug. 13, 2024

(54) **METHODS FOR PREPARING ANTI-INFLAMMATORY HERBAL EXTRACTS COMPRISING *SAMBUCUS NIGRA*, *ECHINACEA PURPUREA* AND *CENTELLA ASIATICA***

(71) Applicant: IZUN PHARMACEUTICALS CORP., New York, NY (US)

(72) Inventors: Amy Debra Rosenbluh, Neve-Tzuf-Halamish (IL); Gabriel Jay Nussbaum, Jerusalem (IL); Avner Rotman, Rehovot (IL)

(73) Assignee: IZUN PHARMACEUTICALS CORP., New York, NY (US)

( * ) Notice: Subject to any disclaimer, the term of this patent is extended or adjusted under 35 U.S.C. 154(b) by 58 days.

(21) Appl. No.: 17/128,118

(22) Filed: Dec. 20, 2020

(65) Prior Publication Data

US 2021/0128661 A1    May 6, 2021

Related U.S. Application Data

(62) Division of application No. 14/385,158, filed as application No. PCT/IB2013/051970 on Mar. 13, 2013, now abandoned.

(60) Provisional application No. 61/610,480, filed on Mar. 14, 2012.

(51) Int. Cl.
*A61K 36/23* (2006.01)
*A61K 36/185* (2006.01)
*A61K 36/28* (2006.01)

(52) U.S. Cl.
CPC ............ *A61K 36/28* (2013.01); *A61K 36/185* (2013.01); *A61K 36/23* (2013.01)

(58) Field of Classification Search
None
See application file for complete search history.

(56) References Cited

U.S. PATENT DOCUMENTS

| | | | |
|---|---|---|---|
| 7,563,466 B2 | 7/2009 | Levine | |
| 2006/0018867 A1 | 1/2006 | Kawasaki et al. | |
| 2007/0292487 A1 | 12/2007 | Loewy | |
| 2008/0020027 A1 | 1/2008 | Loewy | |
| 2011/0151032 A1 | 6/2011 | Levine | |
| 2014/0151789 A1 | 6/2014 | Cotorogea et al. | |

FOREIGN PATENT DOCUMENTS

| | | |
|---|---|---|
| CN | 1356327 | 7/2002 |
| JP | 2001048798 | 2/2001 |
| JP | 2004530698 | 10/2004 |
| JP | 2005179252 | 7/2005 |
| RU | 2317095 | 2/2008 |
| SU | 931188 | 5/1982 |
| WO | 2006024284 | 3/2006 |
| WO | 2009078022 | 6/2009 |
| WO | WO-2009078022 A2 * | 6/2009 ............ A61K 36/23 |
| WO | 20100115 | 1/2010 |
| WO | 2010011541 | 1/2010 |

OTHER PUBLICATIONS

International search report mailed Jul. 17, 2013 for PCT/IB2013/051970 filed Mar. 13, 2013.
Samuels Noah et al, "Effect of an Herbal Mouth Rinse in Preventing Periodontal Inflammation in an Experimental Gingivitis Model: A Pilot Study"; Compendium of Continuing Education in Dentistry, Jamesburg NJ USA, vol. 33, No. 3, Mar. 2012, pp. 204-211.
Glatthaar B et al., "Antiviral activity of a composition of *Gentiana lutea* L., *Primula veris* L., *Sambucus nigra* L., *Rumex spec*, and *Verbana Officinalis* L. (Sinupret) against viruses causing respiratory infections"; European Journal of Integrative Medicine, Elsevier, Amsterdam, NL: vol. 1, No. 4, Dec. 1, 2009; p. 258.
Christensen K. B. et al., "Identification of bioactive compounds from flower of black elder (*Sambucs nigra* L) that activate the human peroxiome proliferator-activated receptor (PPAR) [gamma]"; Phytotherapy Research, John Wiley & Sons Ltd., Chichester GB, vol. 24, No. Suppl 2; Jun. 1, 2010, pp. S129-S132.
Bodinet C. et al., "Effect of oral application of an immunomodulating plant extract on influenza virus type A infection in mince"; Medicinal Aromatic Plants Abstracts, Scientific Publishers, New Delhi, India; vol. 25, No. 2, Apr. 1, 2003.
Kedzia B. et al., "Studies on the biological properties of extracts from *Centella asiatica* (L.) Urban herb"; Medicinal & Aromatic Plants Abstracts, Scientific Publishers, New Delhi, India, vol. 30, No. 5, Oct. 1, 2008.
Office Action Dated Dec. 12, 2016, for Australian Serial No. 2013233943 filed Sep. 10, 2014.
Office Action Dated Oct. 18, 2016, for European Serial No. 13718907.2 Filed Oct. 13, 2014.
Office Action Dated Nov. 1, 2016, for Japanese Serial No. 2014-561570 filed Sep. 4, 2014.
Office Action Dated Dec. 28, 2016, for Russian Serial No. 20141366776 Filed Oct. 14, 2014.
JP Office Action Dated May 9, 2017 for corresponding JP Application Serial No. 2014-561570 filed Sep. 4, 2014.
Minina S.A, "Chemistry and Technology of Phytopreparations" pp. 78, 82-97, 192; 2004.

(Continued)

*Primary Examiner* — Russell G Fiebig
(74) *Attorney, Agent, or Firm* — JMB DAVIS BEN-DAVID (57) ABSTRACT

An aspect of embodiments of the invention relates to providing novel therapeutic compositions comprising herbal extracts of the plant species *Sambucus nigra*, *Echinacea purpurea*, and *Centella asiatica*. The compositions exhibit increased therapeutic activity for treatment of various inflammatory diseases, in particular, inflammatory diseases of mucosa or skin relative to previously identified compositions. In addition the compositions exhibit increased solubility relative to previously identified compositions. In an embodiment of the invention, the ratio of *Sambucus nigra*:*Echinacea purpurea*:*Centella asiatica* is 7:1:2. An embodiment of the invention provides methods for preparing an aqueous therapeutic composition comprising extracts of the aforementioned plant species, using at least two extractions.

6 Claims, 5 Drawing Sheets

(56) References Cited

OTHER PUBLICATIONS

Chueshov V.I. "Industrial Technology of Drugs"; vol. 1. p. 503; 2002.
Russian Office Action dated May 22, 2017, for application No. 2014136776.
Russian Office Action dated Dec. 28, 2016, for Serial No. 2014136776 Filed Oct. 14, 2014.
Chinese Office Action Dated Sep. 29, 2017 for Serial No. 201380014283.9 filed Sep. 15, 2014.
Dongying Jia, Studies on Extraction, Purification, and Chelation, Modification of Naringin, China Doctor and Master Thesis Full-text Database (Doctor), Engineering Technology vol. 1, 2004, No. 01, pp. 22-23, 26-27, 33.
Zhong-zhen Zhao et al., Encyclopedia of Medicinal Plants 3, World Publication Corporation of Shanghai, Feb. 2008, 1st Edition, pp. 404-406.
Ji-xian Hong, Magic echinacea purpurea: the killer of pharyngolaryngitis and cold in 21st century, traidiional Chinese Medicine Classics Press, May 2004, 1st Edition pp. 58-65.
Chinese Office Action dated Feb. 10, 2017, for corresponding application No. 2013800142839, filed Sep. 15, 2014.
European Office Action dated Apr. 19, 2017, for corresponding application No. 13718907.2 filed Oct. 13, 2014.
Amaro et al. (2009) Food Research International 42: 1010-1017.
Olsen et ak. (2008) J. Ethnopharmacol. 117: 500-502.
Part et al. (2012) Intern. J. Molecular Med. 30: 204-210.
Erlund (2004) Nutrition Research 24 : 851-874.
Website document entitled: "Proplene Glycol: Excipient (pharmacology inactive substance)". (available at http://www.drugs.com/inactive/propylene-glycol-270.html).
Website document entitled: "Overview of pharmaceutical excipients used in tablet and capsules." (available at http://drugtopics.modernmedicine.com/drugtopics/Top+news/overview-of-pharmacuetical-excipients-used-tablets.

\* cited by examiner

METHODS FOR PREPARING ANTI-INFLAMMATORY HERBAL EXTRACTS COMPRISING *SAMBUCUS NIGRA*, *ECHINACEA PURPUREA* AND *CENTELLA ASIATICA*

RELATED APPLICATIONS

The is a divisional of U.S. patent application Ser. No. 14/385,158 filed on Sep. 14, 2014; which is the US National Phase of International Patent Application No. PCT/IB2013/051970, filed on Mar. 13, 2013, which in turn claims the benefit of U.S. Provisional Patent Application No. 61/610,480 filed on Mar. 14, 2012; all of which are hereby incorporated by reference in their entirety.

TECHNICAL FIELD

Embodiments of the invention relate to novel compositions of herbal extracts, methods of their preparation, and methods of using the extracts to treat disease.

BACKGROUND

Therapeutic compositions comprising herbal extracts of the plant species *Sambucus nigra, Echinacea purpurea*, and *Centella asiatica* have been described in U.S. Pat. No. 7,563,466.

SUMMARY

An aspect of embodiments of the invention relates to providing novel therapeutic compositions comprising herbal extracts of the plant species *Sambucus nigra, Echinacea purpurea*, and *Centella asiatica*. The compositions exhibit increased therapeutic activity for treatment of various inflammatory diseases, in particular, inflammatory diseases of mucosa or skin relative to previously identified compositions. In addition the compositions exhibit increased solubility relative to previously identified compositions.

An embodiment of the invention provides a composition comprising extracts of the plant species *Sambucus nigra, Echinacea purpurea*, and *Centella asiatica*, the compositions having a concentration of naringenin of greater than or equal to 0.055%. In an embodiment of the invention, the therapeutic composition is soluble in propylene glycol at a concentration of 20%. In an embodiment of the invention, the ratio of *Sambucus nigra:Echinacea purpurea:Centella asiatica* is 7:1:2.

An embodiment of the invention provides methods for preparing an aqueous therapeutic composition comprising extracts of the aforementioned plant species, using at least two extractions.

An embodiment of the invention provides methods for treating diseases, in particular, diseases of the mucosa or the skin, inflammatory diseases, or diseases, conditions or trauma which may be ameliorated by tissue repair, comprising administering compositions comprising extracts of the plant species.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

DETAILED DESCRIPTION

In the following detailed description, new methods of manufacture of compositions comprising herbal extracts will be described. In addition, chemical and biological characterization showing enhanced qualities of new herbal compositions are described. An animal model showing increased anti-inflammatory effect of compositions according to embodiments of the invention are described. A clinical trial showing effect of compositions according to embodiments of the invention in treatment of humans is described. Methods of treatment using the new herbal compositions are provided.

Example 1a: Synthesis of Compositions According to Embodiments of the Invention

Figure 1A:
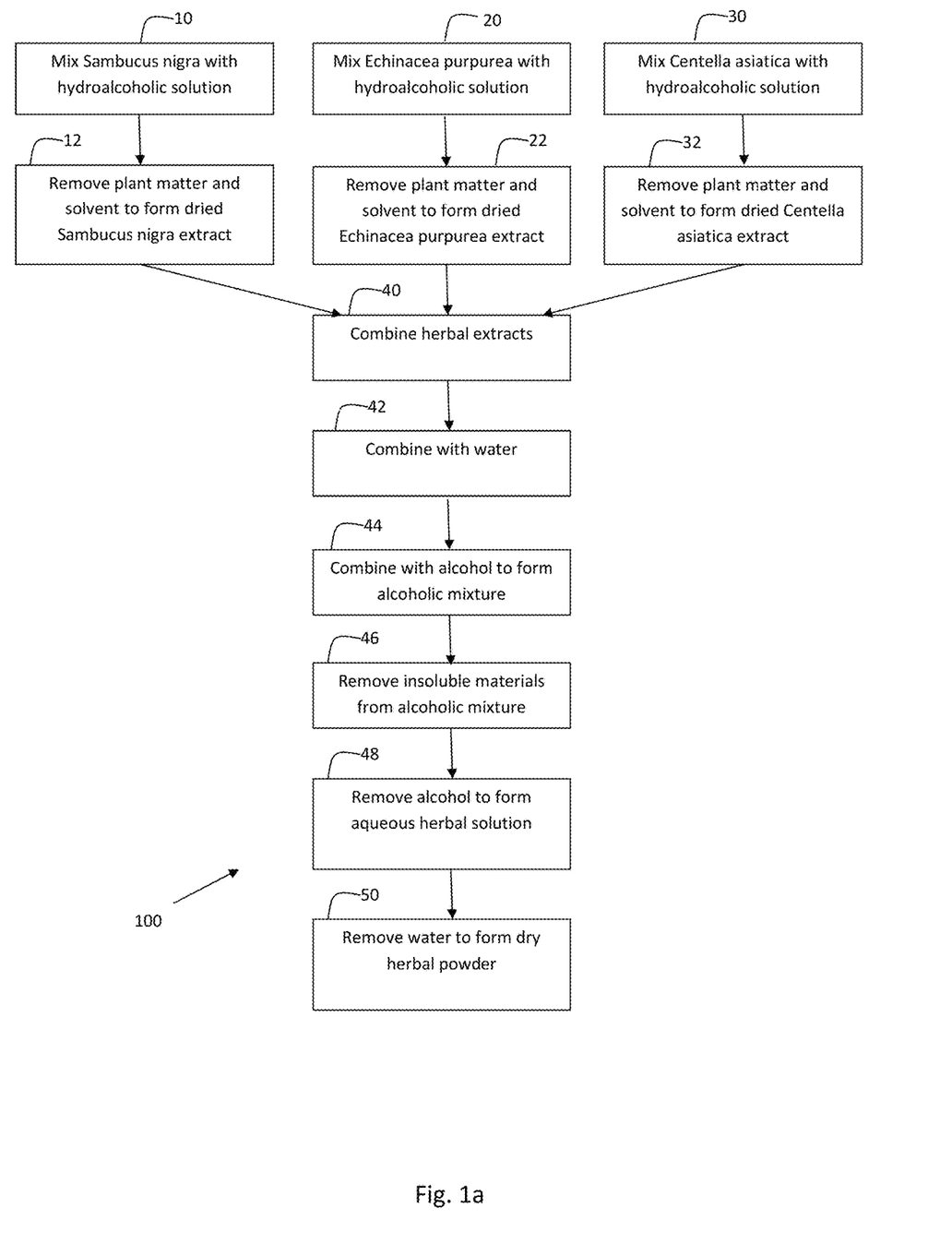
FIGS. 1*a* and 1*b* show flow-diagrams depicting synthetic schemes for manufacture of compositions comprising extracts from the plant species *Echinacea purpurea, Sambucus nigra* and *Centella asiatica* according to embodiments of the invention.

FIG. 1*a* shows a flow-diagram depicting synthetic scheme 100 for synthesizing various compositions comprising extracts from the plant species *Sambucus nigra, Echinacea purpurea*, and *Centella asiatica*. Synthetic scheme 100 comprises blocks 10, 20, and 30 comprising mixing *Sambucus nigra, Echinacea purpurea* and *Centella asiatica* respectively with a hydroalcoholic solution (a solution comprising water and an alcohol). Blocks 12, 22 and 32 comprise removing insoluble plant matter and solvent to form dried extracts of *Sambucus nigra*, *Echinacea purpurea* and *Centella asiatica* respectively. Block 40 comprises combining dried herbal extracts of block 12, 22 and 32.

In an embodiment of the invention, the hydroalcoholic solution of block 10, 20 and/or 30 comprises between 25 and 75% alcohol. In an embodiment, the hydroalcoholic solution of block 10, 20 and/or 30 comprises 70% alcohol. In an embodiment, the alcohol in the hydroalcoholic solution comprises ethanol. In an embodiment, the ratio of solvent to plant in block 10, 20 and/or 30 is between about 6 to about 10 parts by weight of solvent to one part by weight of plant material. In an embodiment, the ratio of solvent to plant in block 10, 20 and/or 30 is between about 8:1 by weight. In an embodiment, the hydroalcoholic solution is mixed for about 8 hours. In an embodiment, the extraction process is multi-stage. In an embodiment, the hydroalcoholic solution is mixed at a temperature of about 30-40 degrees C. (Celsius.) In an embodiment, an excipient is added to the hydroalcoholic solution before removal of solvent and plant matter. In an embodiment, the excipient is a carrier, for example, maltodextrin. In an embodiment the excipient is colloidal anhydrous silica. In an embodiment, the ratio of herbal extract to excipient is about 7:3.

In an embodiment of the invention, solvent is removed in block 12, 22 and/or 32 by spray drying.

In an embodiment of the invention, in block 40, herbal extracts of *Sambucus nigra*:*Echinacea purpurea*:*Centella asiatica* are combined in a weight ratio of 2-15:0.5-3:0.5-3 respectively. In another embodiment, herbal extracts of *Sambucus nigra*:*Echinacea purpurea*:*Centella asiatica* are combined in a weight ratio of 70:10:20 respectively.

Synthetic scheme 100 further comprises block 42, comprising combining water with the combined herbal extract of block 40. In an embodiment, water is combined in a ratio of 3 to 14 liters (L) of water for every kilogram (kg) of herbal extract. In an embodiment, water is combined in a ratio of 9 L of water for every kg of herbal extract. In an embodiment, the water and herbal extract mixture is mixed for about 6 to about 24 hours. In an embodiment the water and herbal extract mixture are mixed for about 12 hours.

Synthetic scheme 100 further comprises block 44, comprising combining alcohol with the mixture formed in block 42. In an embodiment of the invention the alcohol comprises ethanol. In an embodiment, 96% or 100% ethanol is used to form an alcoholic mixture having a concentration of about 50% to about 90% ethanol. In an embodiment, the ethanol is added to reach a concentration of 70% ethanol.

In an embodiment of the invention, the alcoholic mixture of block 44 is stirred for about 6 to about 24 hours, preferably for about 12 hours.

Synthetic scheme 100 further comprises block 46, comprising removing insoluble materials from the alcoholic mixture formed in block 44. In an embodiment of the invention, the insoluble materials are removed from the alcoholic mixture using centrifugation, filtration, settling or a combination of any of these methods.

Synthetic scheme 100 further comprises block 48, comprising removal of alcohol to form an aqueous herbal solution. In an embodiment of the invention, alcohol can be removed by distillation or by evaporation using a rotary evaporator. In an embodiment of the invention, the alcohol is ethanol and is removed using a rotary evaporator at a temperature of less than 30 degrees C.

Synthetic scheme 100 further comprises block 50, comprising removal of water from the aqueous solution of block 48 to form a dry herbal powder. Removal of water may be accomplished, according to embodiments of the invention, using lyophilization (freeze drying) or spray drying.

Figure 1B:
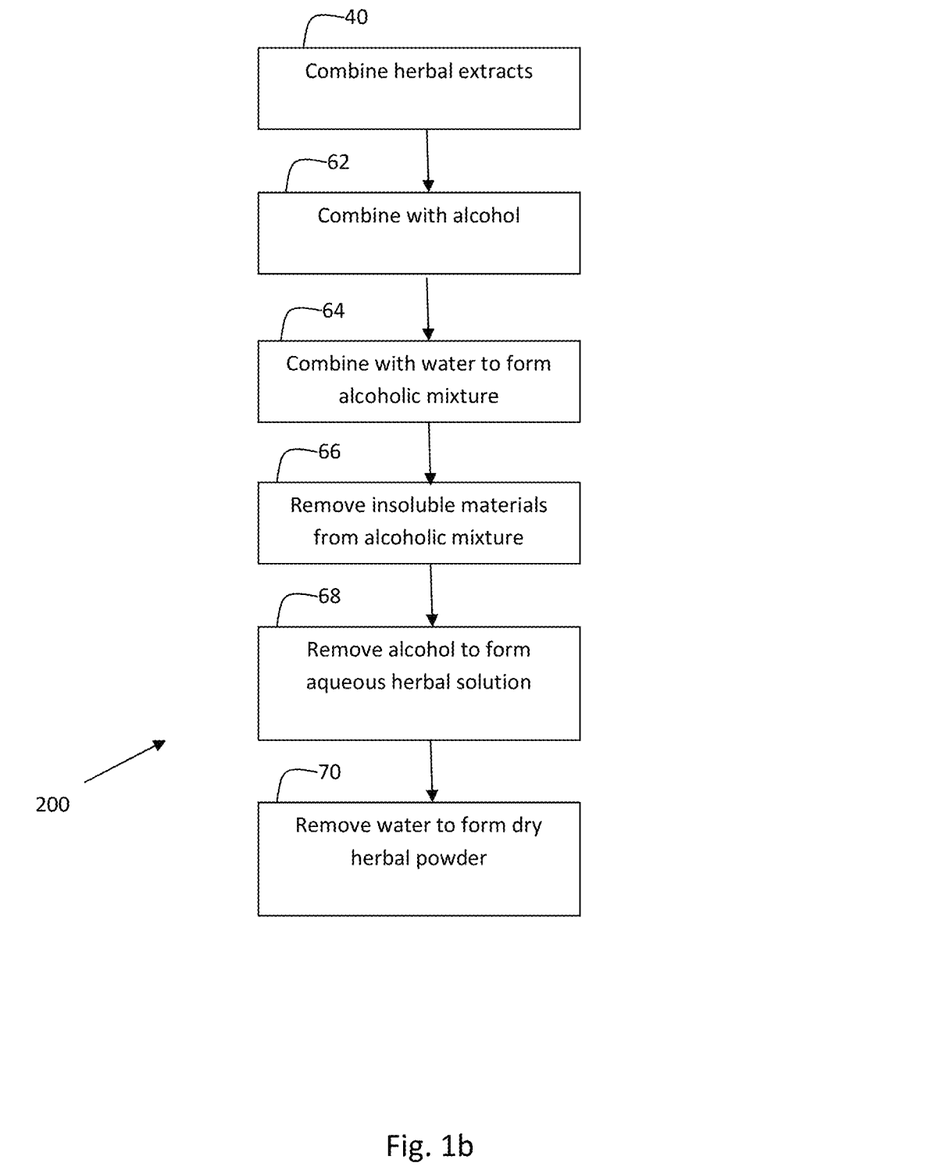

FIG. 1*b* shows a flow-diagram depicting synthetic scheme 200 for synthesizing various compositions comprising extracts from the plant species *Sambucus nigra*, *Echinacea purpurea*, and *Centella asiatica*. Synthetic scheme 200 comprises block 40, comprising combining dried herbal extracts of block 12, 22 and 32 in synthetic scheme 100 as described.

In an embodiment of the invention, in block 40, herbal extracts of *Sambucus nigra*:*Echinacea purpurea*:*Centella asiatica* are combined in a weight ratio of 2-15:0.5-3:0.5-3 respectively. In another embodiment, herbal extracts of *Sambucus nigra*:*Echinacea purpurea*:*Centella asiatica* are combined in a weight ratio of 70:10:20 respectively.

Synthetic scheme 200 further comprises block 62, comprising combining alcohol with the combined herbal extract of block 40. In an embodiment, alcohol is used in a ratio of about 3 to about 14 L alcohol, preferably about 9 L of alcohol for every kg of herbal extract. In an embodiment, the alcohol and herbal extract mixture is mixed for about 12 hours. In an embodiment of the invention the alcohol comprises ethanol. In an embodiment, the ethanol is 96%-100% ethanol.

Synthetic scheme 200 further comprises block 64, comprising combining water with the mixture formed in block 62. In an embodiment, water is used to form an alcoholic mixture having a concentration of about 50% to about 90% ethanol. In an embodiment, the water is used to reach a concentration of 70% ethanol.

In an embodiment of the invention, the alcoholic mixture of block 64 is stirred. In an embodiment, the mixture is stirred for about 6 hours to about 24 hours, preferably for about 12 hours.

Synthetic scheme 200 further comprises block 66, comprising removing insoluble materials from the alcoholic mixture formed in block 64. In an embodiment of the invention, the insoluble materials are removed from the alcoholic mixture using centrifugation, filtration, settling, or any combination of these methods.

Synthetic scheme 200 further comprises block 68, comprising removal of alcohol to form an aqueous herbal solution. In an embodiment of the invention, alcohol can be removed using distillation or evaporation, for example, using a rotary evaporator. In an embodiment of the invention, the alcohol is ethanol and is removed using a rotary evaporator at a temperature of less than 30 degrees C.

Synthetic scheme 200 further comprises block 70, comprising removal of water from the aqueous solution of block 68 to form a dry herbal powder. Removal of water may be accomplished, according to embodiments of the invention, using lyophilization (freeze drying) or spray drying.

Example 1b: Synthesis of Extract N

Synthetic scheme 100 described in example 1a was followed with the following details, in accordance with an embodiment of the invention.

*Sambucus nigra* (flowering tops) was mixed with 70% ethanol (8:1 solvent to plant ratio) according to block 10. Upon removing insoluble plant matter and drying solvent according to block 12, 3.29 kg of dried *Sambucus nigra* extract were formed.

*Echinacea purpurea* (rhizome and roots) was mixed with 70% ethanol (8:1 solvent to plant ratio) according to block 20. Upon removing insoluble plant matter and drying solvent according to block 22, 470 g (grams) of dried *Echinacea purpurea* extract were formed.

*Centella asiatica* (aerial parts) was contacted with 70% ethanol (8:1 solvent to plant ratio) according to block 30. Upon removing insoluble plant matter and drying solvent according to block 32, 940 g of dried *Centella asiatica* extract were formed.

The three dried extracts from the three herbs (ratio of 70:10:20 by weight) were combined in accordance with block 40. In accordance with block 42, 47 L of water were added and the mixture was stirred for 12 hours. 113.9 L of 96% ethanol was added to the mixture to form 160.9 L of a 70% ethanol alcoholic mixture according to block 44. The mixture was filtered in accordance with block 46 and the insoluble material was removed. Ethanol was evaporated in accordance with block 48 and the solution was spray-dried according to block 50 to form 3.2 kg of a dry herbal powder, designated as Extract N. The yield of this process (percentage by weight relative to dried extracts added according to block 40) was 68.7%.

Example 1c: Synthesis of Extract P

The three dried extracts from the three herbs (ratio of 70:10:20 by weight) were combined in accordance with block 40 in scheme 100. Scheme 200 was then followed for production of Extract P. In accordance with block 62, ethanol (100%) was added at a ratio of 9 g of ethanol for every 1 g of dried extract. The mixture was stirred for 12 hours. Water was then slowly added until a final concentration of 70% ethanol was achieved, in accordance with block 64. The mixture was centrifuged in accordance with block 66 and the insoluble material was removed. Ethanol was evaporated using a rotary evaporator under vacuum in accordance with block 68 and the solution was lyophilized according to block 70 to form a dry herbal powder, designated as Extract P. The yield of Extract P (percentage by weight relative to dried extracts added according to block 40) was 75%.

Example 1d: Synthesis of Extract D

The three dried extracts from the three herbs (ratio of 70:10:20 by weight) were combined in accordance with block 40 in scheme 100. An aqueous mixture was formed according to block 42 as described in example 1b and the mixture was mixed for about 17-20 hours. Insoluble materials were removed from the solution by centrifuging the aqueous solution and filtration with a 0.2 micron filter. Water was removed from the filtrate by lyophilization overnight. The dried herbal mixture was designated Extract D.

Example 1e: Synthesis of Extract B

An herbal extract was prepared according to example 1a until block 40. The combined herbal extract was designated Extract B.

Example 1f: Synthesis of Extract M

An herbal extract was prepared according to example 1a (until block 40). 100% ethanol was added to the combined herbal extract and was stirred for 12 hours. Water was added to the ethanolic mixture until the concentration of ethanol was 30%. The ethanol was then removed using a rotary evaporator and then the water was removed by lyophilization. The resulting extract was designated as Extract M.

Example 2: Chemical Analysis of Compositions According to Embodiments of the Invention Extracts according to embodiments of the invention comprises multiple biologically active, including anti-inflammatory, compounds. An HPLC (high-performance liquid chromatography) quantitative analysis was performed to identify chemical differences between Extract D and Extract N.

The HPLC analysis was performed using a Phenomenex Synergi 4 micrometer Hydro-RP 80A column using 0.01 molar phosphoric acid in water and acetonitrile as mobile phase solvents. Detection was performed using a diode array detector.

One of the anti-inflammatory compounds identified in extracts according to embodiments of the invention, which originates from the herb *Sambucus nigra*, is naringenin. A marker was prepared using naringenin (obtained from Sigma) to quantify the amount of naringenin in samples of herbal extracts.

HPLC analysis was performed on Extracts D and N from various batches. Before performing the analysis, Extracts D and N were diluted to 1% solutions in a 50% acetonitrile/50% water solvent. The results are summarized in Table 1 below, with naringenin content expressed in terms of percentage of extract.

TABLE 1

| Batch | Naringenin content (percent of extract) |
| --- | --- |
| Extract D #1 | 0.044 |
| Extract D #2 | 0.02 |
| Extract D #3 | 0.047 |
| Extract N #1 | 0.09 |
| Extract N #4 | 0.09 |
| Extract N #5 | 0.10 |
| Extract N #6 | 0.12 |

Extract P was analyzed and was found to have naringenin content similar to that of Extract N.

As is evident from table 1, naringenin concentration was consistently higher in Extract N than in Extract D, indicating that Extract N has improved anti-inflammatory properties relative to Extract D.

Example 3: In Vitro Testing of Compositions According to Embodiments of the Invention Biological qualities of Extract D and Extract N were compared in a variety of in vitro models.

Example 3a: ICE Assay

ICE (Interleukin-1β-converting enzyme or ICE-caspase-1) is part of a family of cysteine aspartic acid-specific proteases that plays a key role in inflammation. The inhibition of ICE by Extracts D and N was determined for extract concentrations of 2.5, 1.25 and 0.625 mg/ml (milligrams per milliliter) using the following method.

A peptide substrate with the structure Ac-YVAD-AMC is a fluorogenic substrate for ICE, which contains the fluorochrome 7-amino-4-methyl coumarin (AMC). AMC is released from this substrate upon cleavage by ICE. The intensity of the fluorescence signal produced upon cleavage is proportional to the ICE activity present in the sample. A known selective inhibitor of ICE, Ac-YVAD-CHO, was used as a reference for potential inhibition. A black 96-well plate was used with a fluorescence plate reader to detect fluorescence of samples.

Figure 2A:
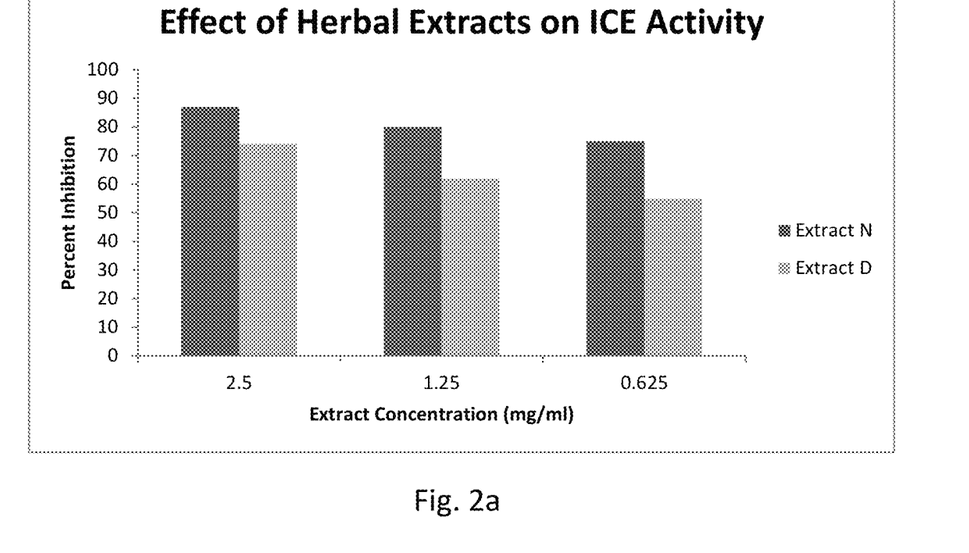
FIG. 2*a* shows a graph comparing effects of an herbal extract according to embodiments of the invention to effects of a conventional extract on inhibition of Interleukin-1β-converting enzyme (ICE) activity, an indicator of inflammation, at various concentrations.

Results of the ICE assay are shown in FIG. 2a. At all concentrations tested, ICE inhibition using Extract N was superior to Extract D. The results suggest that Extract N has an increased anti-inflammatory activity relative to Extract D.

Example 3b: Collagen Release Assay

Collagens are proteins that are abundant in connective tissue and have an important role in wound healing. Agents that cause collagen release in dermal fibroblasts (cells which assist in manufacture of connective tissue) may be useful as wound-healing agents. Effects of Extracts D and N on release of collagen in dermal fibroblasts were tested using the following procedure.

Human foreskin fibroblasts were used in a sandwich ELISA (Enzyme linked immunosorbent assay) based on a pair of antibodies which recognize human type 1 collagen. The antibodies used were Goat anti type 1 Collagen: capture antibody—unlabeled (purchased from Southern Biotech, USA, Cat. #1310-01) and detection antibody-biotin conjugate (purchased from Southern Biotech, USA, Cat. #1310-08.)

Figure 2B:
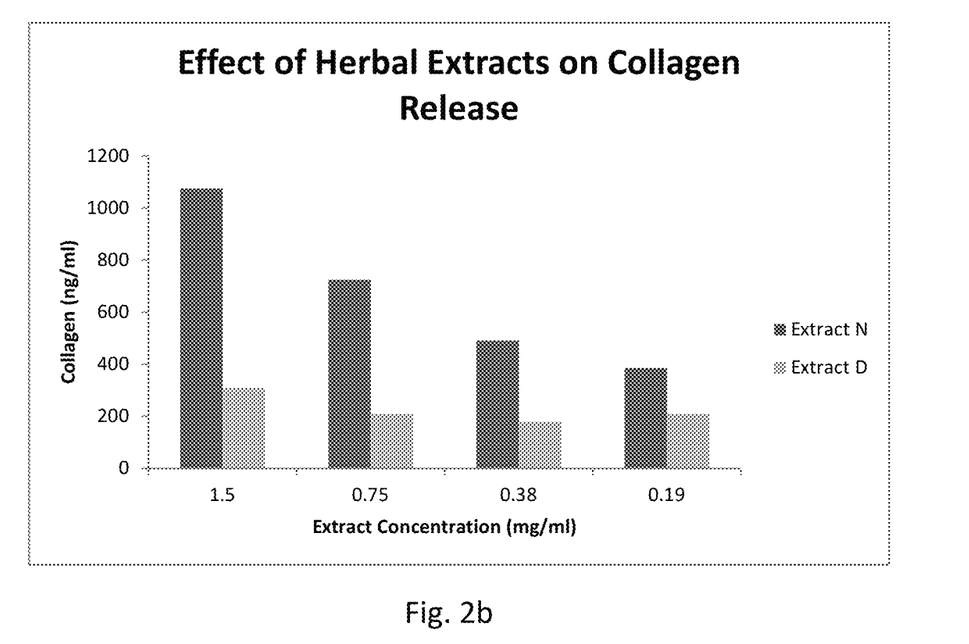
FIG. 2*b* shows a graph comparing effects of an herbal extract according to embodiments of the invention to effects of a conventional extract on collagen release from cells, an indicator of wound healing at various concentrations.

Effects of Extracts D and N on collagen release were tested using concentrations of 1.5, 0.75, 0.38 and 0.19 mg/ml. Results of the collagen release assay are shown in FIG. 2b. In all concentrations tested, Extract N was more effective in inducing collagen production than Extract D, indicating that Extract N has greater wound healing abilities than Extract D.

Example 3c: NFκB Reporter Assay

The NFκB protein plays a key role in inflammation, immune response, cell proliferation and protection against apoptosis.

The murine macrophage cell line RAW264.7 (obtained from the American Type Culture Collection) was transduced with an NF-κB luciferase reporter construct and used in the assay to determine inhibitory effects of Extracts D and N on induction of NF-κB protein in cells containing the NF-κB luciferase reporter gene construct. Lipopolysaccharide (LPS) was used to induce NF-κB luciferase reporter and the extracts were tested for inhibitory activity. Calcein AM (acetomethoxy derivate of calcein) was used as a fluorescent dye to determine RAW264.7 cell number for normalization. As luminescence in the model is correlated to expression of NF-κB protein, inhibition of expression can be determined by correlation with inhibition of luminescence.

Figure 2C:
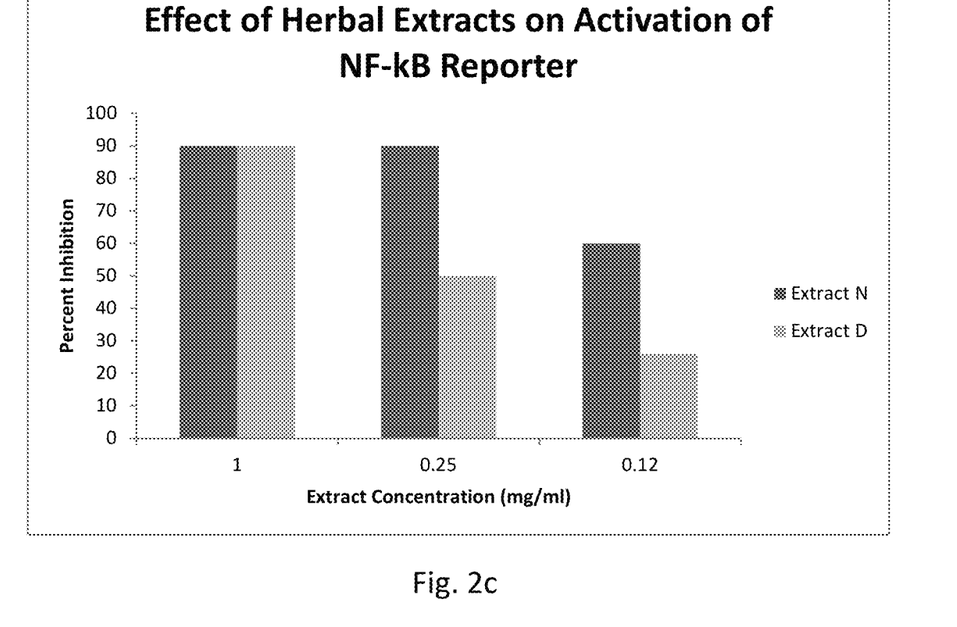
FIG. 2*c* shows a graph comparing effects of an herbal extract according to embodiments of the invention to effects of a conventional extract on inhibition of nuclear factor-kappaB (NFκB), an indicator of inflammation, at various concentrations.

Compositions with high percentage of inhibition in the model indicate their potential use to reduce inflammation by inhibition of NF-κB protein in mammals. The effects of Extracts D and N on NF-κB luciferase reporter at concentrations of 1, 0.25 and 0.12 mg/ml were tested and are shown in FIG. 2c. At the two lower concentrations, Extract N was more effective in inhibition NF-κB luciferase reporter induction than Extract D, indicating that Extract N has enhanced anti-inflammatory properties relative to Extract D and is effective at lower doses.

Example 3d: Nitric Oxide Release Assay

Nitric oxide (NO) is an important physiological messenger and effector molecule that is involved in inflammation. Inhibition of NO production in cells may be indicative of anti-inflammatory qualities of compositions. Extracts D and N were tested for NO inhibitory qualities according to the following assay.

RAW264.7 cells were used for the assay. Presence of NO was measured using the Griess reagent system which measures nitrite, one of two primary stable and non-volatile breakdown products of NO. Nitrite reacts with sulfanilamide and N-1-naphthylethylenediamine dihydrochloride (NED) under acidic (phosphoric acid) conditions to produce a fluorescent azo compound which is detected by a plate reader. LPS was used to induce inflammation in RAW264.7 cells, and inhibition of inflammation was tested using 1.0, 0.5, 0.25 and 0.13 mg/ml of Extracts D and N.

Figure 2D:
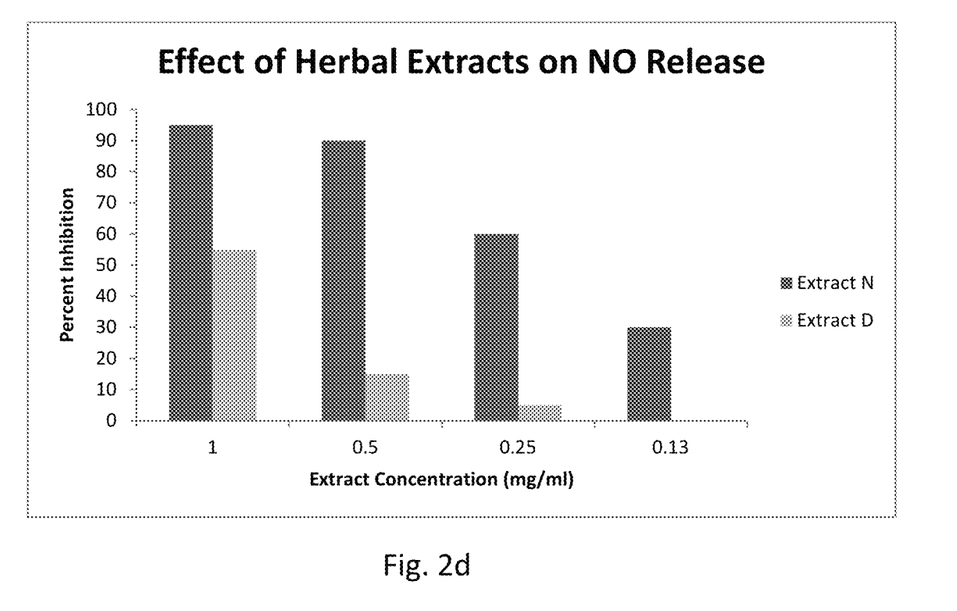
FIG. 2*d* shows a graph comparing effects of an herbal extract according to embodiments of the invention to effects of a conventional extract on inhibition of nitric oxide (NO) activity in cells, an indicator of inflammation, at various concentrations.

Compositions with high percentage of inhibition in the model indicate potential use of compositions to reduce inflammation by inhibition of NO production in mammals. The effects of Extracts D and N on NO production are shown in FIG. 2d. At all concentrations, Extract N was more effective in inhibition of NO production than Extract D, indicating that Extract N has enhanced anti-inflammatory properties relative to Extract D.

Example 3e: IL-11 (Interleukin-11) ELISA Assay

An assay was performed to test the effect of herbal extracts on cytokine induced release of IL-11 in fibroblasts, indicative of a mucosal protective effect. The assay was performed on human gingival fibroblasts.

Gingival fibroblast cell lines were seeded in 150 µl (microliter) of growth medium in 96-well tissue culture plates, with an initial seeding density of $10^4$ cells/well, and cultured for 24 hours. Growth medium was removed and gingival fibroblast cells were then activated with a final concentration of 2.0 ng/ml (nanogram per milliliter) TGF-β (transforming growth factor beta) added in 150 µl of BSA-medium (bovine serum albumin). Herbal extracts at concentrations of 0.5 mg/ml were also added, and the cultures were incubated for an additional 24 hours. TGF-β alone was also tested in order to determine the degree of synergy between the herbal extract and the growth factor.

A sample of conditioned medium (100 µl) was withdrawn for the determination of IL-11 concentration and the gingival fibroblast cells, together with the remaining 501, were tested in a luminescent cell viability assay in order to normalize results. A negative control, without the addition of cytokine, was included. The effect of sample materials on the production of IL-11 was measured by the ELISA assay according to manufacturer's instructions, employing a commercially available kit (R&D Systems, Cat. #DY 218, MN, USA).

The results of IL-11 production in terms of pg/ml (picogram/milliliter) for each extract, both in the presence and absence of TGF-β, were determined. These results were then calculated to determine synergy units, which represent (IL-11 concentration in presence of TGF-β and extract)/(IL-11 concentration in presence of TGF-β alone)+(IL-11 concentration in presence of extract alone.) A value of 1 in the above formula indicates that the value obtained for the TGF-β+the extract, added to the cells together, is the same as the sum of the values obtained for each of these added to the gingival fibroblast cells separately. This is an additive effect. Values of greater than 1 indicate synergistic effect of herbal extract.

TABLE 2

| Extract sample | Synergy Units |
|---|---|
| B | 2.2 |
| D | 1.5 |
| M (a) | 0.9 |
| M (b) | 0.9 |
| N (a) | 1.8 |
| N (b) | 1.8 |
| P (a) | 1.9 |
| P (b) | 1.7 |

As can be seen in table 2, Extracts N and P showed synergistic activity, but Extract M did not show synergistic activity.

Example 4: In Vivo Testing of Compositions According to Embodiments of the Invention Using a Model of Oral Mucositis (OM) in Hamsters Male Syrian Golden Hamsters ("hamsters") weighing approximately 95 g were randomly assigned to two vehicle control groups of eight hamsters each and four test article groups of six hamsters each. On study day 0, each hamster was given an acute radiation dose of 40 Gy (gray) directed to the left buccal cheek pouch. Test articles were administered topically three times daily on days −1 (the day before radiation dose) to 20. Hamster condition was assessed daily and body weights were measured once daily from day −1 to day 25. Mucositis was evaluated on days 7, 10, 13, 16, 19, 22 and 25. The duration and severity of mucositis were compared between treatment groups and the untreated control group to determine the impact of the test article on the course of mucositis.

Mucositis in hamsters was scored according to table 3:

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray appearance due to pseudomembrane. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth). |

Two vehicle control groups were given either saline solution or propylene glycol (PG). The four treatment groups were administered treatments as follows:
Group 1: Extract B 1% in 100% PG
Group 2: Extract M 1% in 100% PG
Group 3: Extract N 1% in 100% PG
Group 4: Extract N 1% dissolved in saline followed by one minute vortex.

Figure 3:
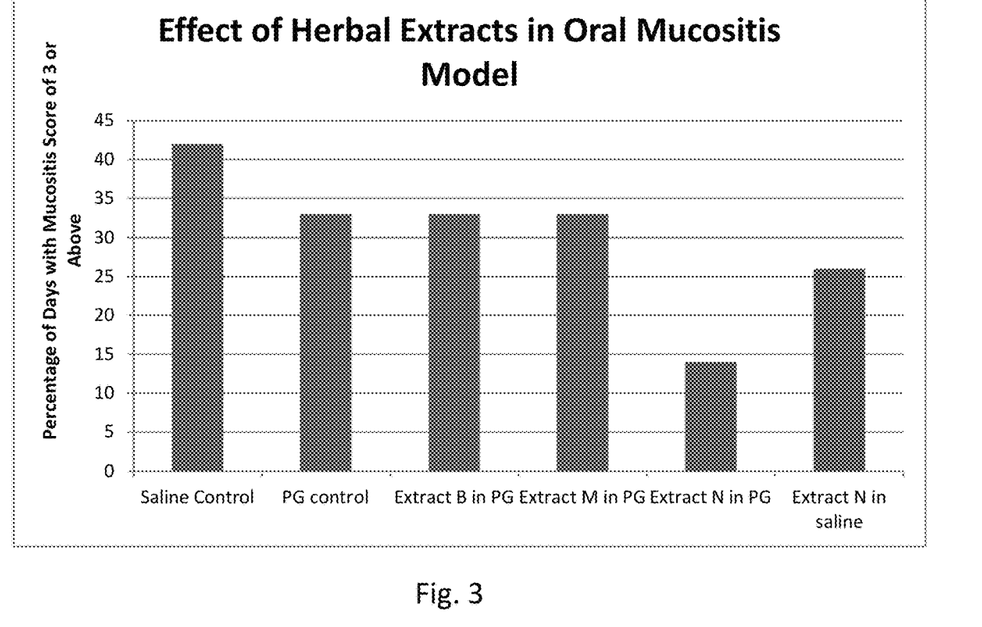
FIG. 3 shows a graph depicting beneficial effect of formulations of extracts according to embodiments of the invention on reduction of mucositis scores in hamsters in a model of radiation-induced oral mucositis.

0.2 ml of the tested compositions were administered three times daily to each hamster. The total number of days in which a hamster exhibited an elevated score above three was summed for each group and expressed as a percentage of the total number of days scored for each group. The results are shown in FIG. 3.

Extract N in saline had a significant (p=0.024) effect on reducing mucositis score relative to the saline control group. Similarly, Extract N in PG had a significant (p=0.003) effect on reducing mucositis score relative to the PG control group. Extracts B and M did not show reduction in hamster scores below 3 relative to the PG control group.

The results of this trial indicate that Extract N may be effective in treatment of OM in humans. This effect was evident in formulations of Extract N based on either water (saline solution) or PG.

Example 5: Enhanced Solubility of Compositions According to Embodiments of the Invention Solubility testing was performed to differentiate between Extract B and Extract N.

Extract solutions were prepared using Extract B and N at concentrations of 1% (grams per liter) in water. During stirring, both solutions were cloudy. Extract B had particles that could be discerned by eye which floated around during stirring in a fairly clear solution. Extract N had non-discernable particles although the solution was cloudy, giving a more homogeneous dispersion. Turbidity was measured using a Micro 100 Turbidimeter manufactured by HF Scientific and was expressed in terms of Nephelometric Turbidity Units (NTU). As can be seen in the table below, there was a significant difference in the turbidity of the two formulations, with the larger particles in B settling out much more quickly than those in N.

TABLE 4

| Time | B turbidity (NTU) | N turbidity (NTU) | B turbidity % relative to time 0 | N turbidity % relative to time 0 |
|---|---|---|---|---|
| 0 min | 285 | 410 | — | — |
| 15 min | 215 | 410 | 75 | 100 |
| 30 min | 154 | 401 | 54 | 98 |
| 55 min | 128 | 378 | 45 | 92 |
| 90 min | 119 | 376 | 42 | 92 |
| 18 hours | 33.5 | 137 | 12 | 33 |

Solutions in 100% PG were prepared at a concentration of 5% (grams per liter). Extract N appeared to dissolve completely but Extract B was cloudy. Turbidity was measured after stirring and was determined to be 385 NTU for Extract B and 14.7 NTU for Extract N. After sitting overnight, large quantities of sediment settled out of the suspension of Extract B, and no sediment was visible in the clear Extract N mixture.

These tests indicate that Extract N has higher solubility and forms more stable suspensions than Extract B in water. In addition, PG solutions can be formulated with extract N at 5-20% concentration (by weight) whereas extract B does not provide stable solutions at these concentrations. Extract N can be viably formulated in PG without the need for additional solubilizing agents.

Example 6a: Pharmaceutical Compositions Comprising Extracts According to Embodiments of the Invention 2.601 kg of Extract N was stirred for 12 hours with 10.379 kg of PG and 26.01 g sucralose to form a concentrate solution. 2.5 g of concentrate solution was mixed with 47.5 ml of saline solution to prepare a mouth rinse.

Example 6b: Pharmaceutical compositions comprising extracts according to additional Embodiments of the Invention In additional embodiments of the invention, the composition of the present invention further comprises an extract of the plant species *Hypericum perforatum* and *Commiphora molmol, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtilltus, Melissa officinalis, Allium sativum, Camellia sinensis, Hamamelis virginiana* or *Krameria triandra*.

In additional embodiments of the invention, pharmaceutical compositions may be prepared in the form of patches, ointments, pastes, lotions, creams, lozenges, candies, chewing gums, solutions, gels, foams and sprays. Pharmaceutical compositions may be prepared, according to embodiments of the invention, in the form of immediate release or delayed release compositions.

Example 7a: Methods of Treatment Using Compositions According to Embodiments of the Invention OM is among the most frequently reported and potentially most debilitating condition associated with cancer chemotherapy and radiation treatment, ranging in incidence from 10%-75% in patients receiving chemotherapy or radiotherapy, 70-90% in bone marrow transplant recipients and >95% of patients receiving combination radiation and chemotherapy for head and neck cancers (HNC). OM has been associated with increased analgesic and antibiotic use, febrile days, need for gastric tube or parenteral nutrition, length of hospital stay, unplanned and emergency room visits and total medical expenses, all of which have a negative impact on health and economic outcomes. Approximately 500,000 patients develop OM in the United States annually, and it is considered largely unpreventable.

A double blind, randomized, placebo controlled, fixed-dose, comparative study testing effects of mouth rinse according to example 6a in OM is performed in patients undergoing CRT (chemo-radio therapy) for HNC. Patients are randomized to receive either active mouth rinse or a placebo according to a 1:1 randomization schedule. Rinse dose is 15 ml of 1% oral rinse, as described in example 6, at a frequency of three times daily. The placebo is prepared using PG, sucralose and food coloring, diluted in saline.

About 104 subjects receive treatment for approximately 7-9 weeks, concurrently with CRT and extended until resolution of severe mucositis. Subjects are scheduled to receive a continuous course of external beam irradiation delivered either through intensity modulated radiotherapy or 3D planning. The cumulative prescription dose is between 50-70 Gy. A minimum of 25% of the oral cavity receives a dose of 50 Gy or more. Radiotherapy is delivered concurrently with cisplatin chemotherapy in a dose of either 60-100 mg/m2 (milligrams per square meter), administered once every 21 days, or 30-40 mg/m2, administered once a week.

Safety is evaluated by general toxicity based on vital signs and physical examinations. Efficacy is evaluated by proportion of patients in active treatment group versus placebo group scoring a 3-4 according to WHO (World Health Organization) oral toxicity scale for OM at a cumulative radiation dosage of 50 Gy.

WHO oral toxicity scale for OM is as follows: Grade 0: No mucositis or mucosal lesions. Grade 1: erythema, mucosal sensitivity and pain. Grade 2: Ulceration, ability to eat solid foods. Grade 3: Ulceration, oral intake limited to fluids. Grade 4: Ulceration, oral feeding is impossible.

Figure 4:
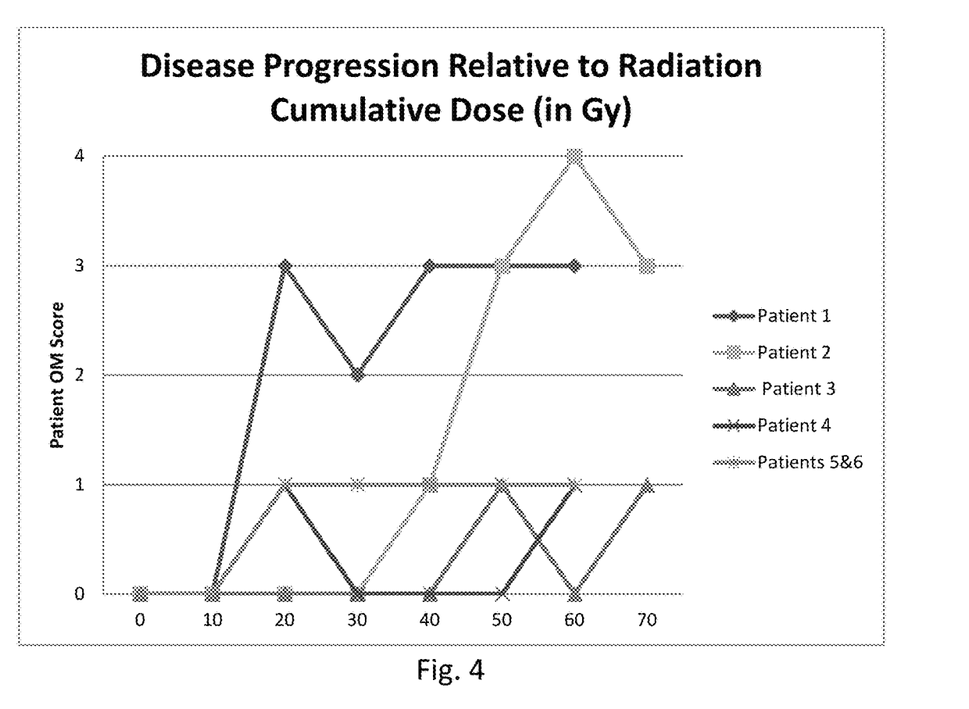
FIG. 4 shows a graph depicting effect of compositions according to embodiments of the invention on oral mucositis scores in six human patients.

In an open-labeled section of the trial, seven patients were treated with the pharmaceutical composition described in Example 6a. A graph showing OM score relative to cumulative radiation dose is shown in FIG. 4. Patients 5 and 6 had overlapping scores during the course of treatment and are represented by one line.

In the patient population tested, approximately 75% of patients who receive equivalent cumulative doses of radiation to the oral cavity are expected, based on historical data, to develop grade 3-4 OM. One of the patients dropped out of the trial after a very short duration of treatment due to an apparent allergic reaction to one of the components in the composition. Out of the remaining 6 patients, 4 were considered to have responded favorably to treatment, as the scoring in these patients did not exceed 1 throughout the treatment. One additional patient was considered a partial responder as the patient's development of OM was delayed until after the patient received a cumulative dose of >40 Gy of radiation.

The results of the open-label section of the trial show that compositions prepared according to embodiments of the invention are effective in treating patients at risk of developing OM, including patients who have received radiation to the oral cavity. Similar results are expected from the complete trial.

Example 7b: Use of Compositions According to Embodiments of the Invention in a Patient Suffering from OM A patient aged about 80 years old suffering from pancreatic cancer was treated intermittently with chemotherapy and radiation for a period of 3 years. The patient was diagnosed as suffering from OM and was treated with composition Q (preparation described below) for a period of about 2-3 weeks. No significant improvement of OM was recognized.

Composition Q was prepared using the following method. Ethanolic extractions of herbs *Sambucus nigra, Echinacea purpurea* and *Centella asiatica* were prepared and then combined in a ratio of 85:5:10. The blend was then extracted with water in a ratio of 9 L of water to every 1 kg of combined herbal extract. The insoluble material was removed and the soluble phase was filtered. The soluble phase was then formulated into a composition Q by combining with water, disodium EDTA, sodium benzoate, cetyl pyridinium chloride monohydrate, PEG-40 Hydrogenated Castor Oil 90%, S-Lactic Acid, sorbitol, PG, flavoring and erioglaucine. The concentration of solid content in the soluble phase in the composition Q was 1%.

After 2-3 week period, administration of composition Q was stopped, patient was then administered a composition according to example 6. The patient experienced a measurable decrease of pain and reduction of size of ulcerated areas within a 25 hour period.

In addition to treating OM, other diseases related to inflammation of the mucosa may be treated using extracts according to embodiments of the invention. The mucosa treated using extracts according to embodiments of the invention may include buccal, esophageal, gastric, intestinal, nasal, olfactory, oral, bronchial, uterine, endometrial, vaginal or penile mucosa. Inflammatory diseases according to embodiment of the invention include inflammatory bowel disease, radiation induced proctitis and atrophic vaginits.

Compositions comprising extracts according to embodiments of the invention may be used for treatment or prevention of a variety of diseases and indications. In an embodiment of the invention, the composition is intended for use in the treatment of diseases of the oral mucosa. In an embodiment of the invention, the therapeutic composition is intended for use in the treatment of an oral mucosal disease selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes.

In an embodiment of the invention, the therapeutic composition is intended for use in the treatment of skin lesions. In an embodiment of the invention, the therapeutic composition is intended for use in the treatment of dermal trauma. In another preferred embodiment, the therapeutic composition is intended for use in the treatment of insect bites and other local, superficial irritations.

In an embodiment of the invention, the therapeutic composition is intended for use in the treatment of anal lesions. In an embodiment of the invention, the therapeutic composition is intended for use in the treatment of an anal lesion associated with a condition selected from the group consisting of anal fissures, hemorrhoids and non-specific irritation.

In an embodiment of the invention, the therapeutic composition is intended for use in the treatment of vaginal lesions. In an embodiment of the invention, the therapeutic composition is intended for use in the treatment of a vaginal lesion associated with atrophic vaginitis.

Embodiments of the invention provide methods for treatment comprising administering between 1 mg and 1.5 g of an herbal extract per day. In embodiments of the invention, the daily dosage is 625 mg/day. In embodiments, the daily dosage is 450 mg/day. Another embodiment is 900 mg/day.

There is further provided in accordance with an embodiment of the invention, a method for preparing an aqueous therapeutic composition comprising: combining hydroalcoholic herbal extracts of *Sambucus nigra*, *Echinacea purpurea*, and *Centella asiatica* with water to form an aqueous mixture; combining the aqueous mixture with an alcohol to form an alcoholic mixture having a concentration of over 50% alcohol; separating insoluble materials and alcohol from alcoholic mixture to produce an aqueous therapeutic composition. Optionally, the alcoholic mixture comprises about 70% alcohol. Optionally, the aqueous therapeutic composition is further dried to form a dried therapeutic composition. Optionally, the alcohol is ethanol. Optionally, insoluble materials are separated from the alcoholic mixture using centrifugation, filtration or settling. Optionally, alcohol is separated from the alcoholic mixture using vacuum. Optionally, the aqeuous therapeutic composition is dried by spray drying or freeze drying. Optionally, the method further comprises combining the dried therapeutic composition with at least one pharmaceutically acceptable excipient. Optionally, the excipient is selected from the group consisting of: propylene glycol, polyethylene glycol, glycerin and essential oil. Optionally, hydroalcoholic herbal extracts of *Sambucus nigra*, *Echinacea purpurea*, and *Centella asiatica* are prepared by mixing the plant matter in a solvent comprising about 70% alcohol. Optionally, the plant matter is mixed for about 8 hours. Optionally, the ratio of plant matter to solvent is approximately 1:8. Optionally, the method further comprises removing solvent from the mixture of plant matter and solvent to form a hydroalcoholic herbal extract.

There is further provided in accordance with an embodiment of the invention an herbal extract comprising hydroalcoholic herbal extracts of each of *Sambucus nigra*, *Echinacea purpurea*, and *Centella asiatica*, the extract comprising naringenin concentration of greater than or equal to 0.055%. Optionally, the herbal extract has solubility in a 20% solution in propylene glycol. Optionally, the ratio of *Sambucus nigra*:*Echinacea purpurea*:*Centella asiatica* is about 7:1:2.

There is further provided in accordance with an embodiment of the invention a pharmaceutical composition comprising an herbal extract comprising hydroalcoholic herbal extracts of each of *Sambucus nigra*, *Echinacea purpurea*, and *Centella asiatica*, the extract comprising naringenin concentration of greater than or equal to 0.055%. Optionally, the pharmaceutical composition further comprises a pharmaceutically acceptable carrier. Optionally, the carrier comprises propylene glycol. Optionally, the pharmaceutical composition according is in the form of a mouth rinse, patch, ointment, paste, lotion, cream, lozenge, candy, chewing gum, solution, gel, foam or spray.

There is further provided in accordance with an embodiment of the invention a method for treating a disease comprising administering a pharmaceutically acceptable amount of a pharmaceutical composition comprising an herbal extract comprising hydroalcoholic herbal extracts of each of *Sambucus nigra*, *Echinacea purpurea*, and *Centella asiatica*, the extract comprising naringenin concentration of greater than or equal to 0.055%. Optionally, the disease is a disease of the mucosa or of the skin. Optionally, the disease is an inflammatory disease. Optionally, the disease is ameliorated by tissue repair. Optionally, the disease is selected from the group consisting of oral mucositis, inflammatory bowel disease, radiation induced proctitis, atrophic vaginits, periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes. Optionally, the amount of herbal extract administered is between 1 mg and 1.5 g per day.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

We claim:

1. A process for the manufacture of a combined herbal extract comprising:
   a. mixing *Sambucus nigra* flowering tops, *Echinacea purpurea* rhizome and *Centella asiatica* aerial parts each individually with first hydroalcoholic solutions comprising 70% ethanol and 30% water at 30-40 degrees C. for about 8 hours, wherein the ratio of first hydroalcoholic solution to each of *Sambucus nigra, Echinacea purpurea* and *Centella asiatica* is between 6:1 and 10:1;
b. removing insoluble plant matter from the first hydroalcoholic solutions of step a;
c. drying each of the hydroalcoholic solutions of step b to form herbal extracts;
d. combining the herbal extracts with water and mixed with water for between 6 and 24 hours, and then with an alcohol, to form a second hydroalcoholic solution comprising 70% ethanol and mixed for between 6 and 24 hours, wherein the ratio of *Sambucus nigra: Echinacea purpurea: Centella asiatica* herbal extracts is about 2-15:0.5-3:0.5-3, in a ratio of about 1 kg herbal extracts to 34 L of second hydroalcoholic solution, for between 6 to 24 hours;
e. removing insoluble material from the second hydroalcoholic solution and
f. drying the second hydroalcoholic solution to form a combined herbal extract.

2. The process according to claim 1 wherein drying the second hydroalcoholic solution is performed through lyophilizaton or spray-drying.

3. The process according to claim 1 wherein the ratio of *Sambucus nigra: Echinacea purpurea: Centella asiatica* in the herbal extracts combined in step d is 7:1:2.

4. The process according to claim 1 wherein the ratio is 8:1.

5. The process according to claim 1 wherein the herbal extracts are mixed with water for 12 hours.

6. The process according to claim 1 wherein the second hydroalcoholic solution is mixed for 12 hours.

* * * * *